United States Patent [19]

Bernard

[11] Patent Number: 4,459,298
[45] Date of Patent: Jul. 10, 1984

[54] METHOD OF SUPPRESSING APPETITE

[75] Inventor: Patrick S. Bernard, Chatham, N.J.

[73] Assignee: Ciba-Geigy Corporation, Ardsley, N.Y.

[21] Appl. No.: 426,011

[22] Filed: Sep. 28, 1982

[51] Int. Cl.³ .............................................. A61K 31/47
[52] U.S. Cl. ................................................... 424/258
[58] Field of Search ......................... 424/258; 546/82

[56] References Cited

U.S. PATENT DOCUMENTS

| | | | |
|---|---|---|---|
| 3,890,324 | 6/1975 | Katner | 424/232 |
| 4,076,818 | 2/1978 | Vogt | 424/251 |
| 4,112,096 | 9/1978 | Vogt | 424/251 |
| 4,112,098 | 9/1978 | Vogt | 424/251 |
| 4,146,621 | 3/1979 | Voorhees | 424/240 |
| 4,164,578 | 8/1979 | Vogt | 424/115 |
| 4,179,561 | 12/1979 | Vogt | 424/250 |
| 4,268,516 | 3/1980 | Lombardino et al. | 424/273 P |
| 4,312,870 | 1/1982 | Yokoyama | 424/258 |

FOREIGN PATENT DOCUMENTS 35270 1/1981 European Pat. Off. .
22078 1/1981 European Pat. Off. .

OTHER PUBLICATIONS

Chem. Abst. 96, 97082(w), (1982), Czernik et al.
Life Sciences 30, 245-252, 363-372, (1982).
Neuropharmacology 21, 483-486, (1982).
Science 217, 77-79, (1982).
J. Med. Chem. 25, 337-339, (1982).

Primary Examiner—Douglas W. Robinson
Attorney, Agent, or Firm—Norbert Gruenfeld

[57] ABSTRACT

Certain pyrazolo[4,3-c]quinolin-3-ones, e.g. those of the formula

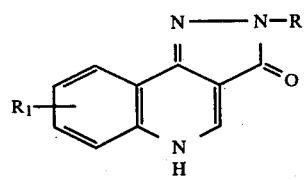

wherein $R_1$ is hydrogen, alkyl or alkoxy with up to 4 carbon atoms each, hydroxy, fluoro, chloro, bromo or trifluoromethyl; and R is phenyl, fluorophenyl or pyridyl; or pharmaceutically acceptable salts thereof; and pharmaceutical compositions comprising above compounds are useful for suppressing appetite in mammals.

6 Claims, No Drawings

METHOD OF SUPPRESSING APPETITE

BACKGROUND AND SUMMARY OF THE INVENTION

The pyrazolo[4,3-c]quinolin-3-ones of formula I, and pharmaceutical compositions thereof, have been disclosed as psychoactive agents in e.g. U.S. Pat. No. 4,312,870, Life Sciences 30, 363–372 (1982), and J. Med. Chem. 25, 337 (1982). Illustrative of the state of the art, is the anorectic activity disclosed for inosine in Science 217, 77 (1982), and disclosed for 1-N-alkyl-pyrazolidin-3-ones in European Patent Application No. 35,270.

The compounds of formula I have been found to possess anorectic (appetite suppressant) effects without or with only minimal overt side effects, and are thus unexpectedly useful anorectic agents for controlling and reducing food intake, appetite and body weight (e.g. in obesity) in mammals.

DETAILED DISCLOSURE OF THE INVENTION

The present invention is specifically directed to a novel method of controlling and suppressing appetite in mammals which comprises the enteral or parenteral, preferably enteral, administration of an appetite-suppressant compound of formula I, or of a pharmaceutical composition comprising an effective amount of an appetite suppressant compound of formula I

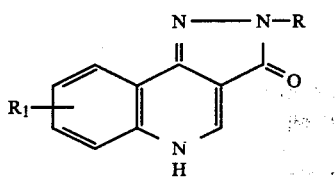

or a tautomer thereof wherein $R_1$ is hydrogen, alkyl or alkoxy with up to 4 carbon atoms each, hydroxy, fluoro, chloro, bromo or trifluoromethyl; and R is phenyl, fluorophenyl or pyridyl; or a pharmaceutically acceptable salt thereof in combination with one or more pharmaceutical carriers.

Preferred as appetite-suppressant agents are the compounds of formula I wherein $R_1$ is hydrogen or 7- or 8-(alkyl or alkoxy with up to 4 carbon atoms, fluoro, chloro or trifluoromethyl) and R is phenyl, fluorophenyl or pyridyl; and pharmaceutically acceptable salts thereof. The alkyl and alkoxy groups represented by $R_1$ are advantageously methyl and methoxy respectively.

Further preferred as appetite suppressant agents are the compounds of formula I wherein $R_1$ is hydrogen or 8-fluoro; R is phenyl, p-fluorophenyl or 3-pyridyl; and pharmaceutically acceptable salts thereof.

Particularly preferred as appetite suppressant agents are the compounds of formula I wherein $R_1$ is hydrogen or 8-fluoro; R is phenyl or p-fluorophenyl; and the sodium, hydrochloride and mesylate salts thereof.

Preferred in context of the present invention is the method of suppressing appetite consisting in the enteral administration of the preferred appetite-suppressant compounds of formula I or pharmaceutical formulations comprising said preferred compounds of formula I described above.

The compounds of formula I above and the pharmaceutically acceptable salts and tautomers thereof, their properties, methods of preparation, and pharmaceutical compositions thereof are disclosed in U.S. Pat. No. 4,312,870.

Pharmaceutically acceptable salts of the compounds of instant formula I or the tautomeric hydroxy forms thereof are preferably the alkaline or alkaline earth metal salts, e.g. the sodium, potassium, calcium and magnesium salts, also the acid-addition salts, e.g. the hydrochloride, sulfate, phosphate, maleate, fumarate and methanesulfonate (mesylate) salts; most preferred are the sodium, hydrochloride and mesylate salts.

The compounds of formula I are formulated into appetite-suppressant pharmaceutical compositions comprising an effective amount of a said pyrazoloquinoline of formula I or a salt thereof in combination with conventional excipients or carriers suitable for either enteral or parenteral, such as oral, rectal or intravenous administration. Preferred are tablets, dragees and gelatin capsules comprising the active ingredient together with (a) diluents, e.g., lactose, dextrose, sucrose, mannitol, sorbitol, cellulose, calcium phosphates and/or glycine, (b) lubricants, e.g., silica, talcum, stearic acid, its magnesium or calcium salt and/or polyethyleneglycol; for tablets also, (c) binders, e.g., magnesium aluminum silicate, starch paste, gelatin, tragacanth, methylcellulose, sodium carboxymethylcellulose and/or polyvinylpyrrolidone; if desired, (d) disintegrants, e.g., starches, agar, alginic acid or its sodium salt, or effervescent mixtures and/or, (e) absorbents, colorants, flavors and sweeteners. Dragee or tablet cores may be provided with suitable coatings, which may be resistant to gastric juices. Coating solutions are, for example, concentrated aqueous sugar solutions, which may contain gum arabic, polyvinylpyrrolidone, polyethylene glycol, talcum and/or titanium dioxide. Said resistant coatings are obtained with lacquer solutions in organic solvents, such as shellac, acetylcellulose phthalate or hydroxypropylmethylcellulose phthalate in ethanol and the like. Dyestuffs or pigments may be added for identification of brand name and dose. Capsules are either made from hard gelatin, or they are soft, closed capsules made from gelatin and a softener, e.g., glycerin or sorbitol. The hard capsules contain either uncompressed powder mixtures, e.g. those mentioned under (a) and (b), or granulates similar to those used for tablets. In the soft capsules said active ingredients are preferably dissolved or suspended in suitable liquids, such as fatty oils, paraffins or polyethylene glycols. Suppositories are advantageously solid, fatty emulsions or suspensions, containing the active ingredient, for example, in natural or synthetic triglycerides, paraffins, waxes and/or polyethylene glycols.

Compositions for parenteral administration are preferably aqueous solutions or suspensions of said active substances, but also oily solutions or suspensions thereof, e.g., in natural or synthetic fatty oils, such as sesame oil or ethyl oleate, in suitable ampules.

Said compositions may be sterilized and/or contain adjuvants, such as preserving, stabilizing, wetting or emulsifying agents, solution promoters, salts for regulating the osmotic pressure and/or buffers. They may also contain other therapeutically valuable substances, and are prepared according to conventional mixing, granulating or coating methods respectively. They may contain from about 10 to 95%, preferably from about 20 to 70% of the active ingredient. Individual unit dosages thereof for a mammal of about 50–70 Kg weight may contain preferably between about 10 and 200 mg., advantageously about 20 to 100 mg of said active ingredients.

The new method of suppressing appetite can be demonstrated in animal tests, using mammals, such as rats, monkeys or dogs as test subjects. Said compositions are administered in such tests either enterally, e.g. orally or intraperitoneally, or parenterally, e.g. intravenously. The applied dosage may range between about 1 and 200 mg/Kg/day, preferably between 1 and 100 mg/Kg/day, advantageously between about 5 and 50 mg/Kg/day.

Appetite-suppressant effects are observed, for example, according to a procedure using male Wistar rats which are maintained at 80% of normal body weight by dietary-, but not water-restriction. The rats are trained to press a lever within a conditioning chamber, also containing a liquid dipper, a house light and a grid-floor. The chamber is situated in a sound-attenuated box during testing in order to mask any extraneous auditory cues. The schedule is a Variable Interval (VI) schedule of 30 seconds lasting for 30 minutes, during which a sweetened, condensed milk reinforcement is delivered following the first lever press after an average of 30 seconds have elapsed. A drug-induced decrease of the response rate for food reinforcement is taken as an indication of an appetite-suppressant effect in the absence of any performance deficit. Test agents are suspended in 3% cornstarch and administered intraperitoneally 30 minutes prior to the experimental session. Responses made during the three control sessions prior to treatment sessions are averaged and serve as the control response value for each animal.

Illustrative of the invention 2-phenylpyrazol[4,3-c]quinolin-3(5H)-one reduces the response rate for food reinforcement in the rat by about 45% at a dose of 20 mg/Kg i.p and about 58% at a dose of 80 mg/Kg i.p. Similarly, 2-(p-fluorophenyl)-8-fluoropyrazolo[4,3-c]quinolin-3(5H)-one reduces the response rate by about 22% at 40 mg/Kg i.p. and by about 73% at a dose of 80 mg/Kg i.p.

The absence of a performance deficit is determined by rotorod performance as follows:

Male Wistar rats are fasted for 18 hours but allowed water ad libitum prior to testing. Rotorod performance is assessed using a rat treadmill (16 rpm). Any animal which fails to remain on the bar for 30 seconds, in at least one of three trials, is considered to have a performance deficit. Test agents are suspended in 3% cornstarch and administered e.g. intraperitoneally 45 to 60 minutes prior to testing.

No rotorod performance deficit is detected in the rat upon administration of 2-phenylpyrazolo[4,3-c]quinolin-3(5H)-one or 2-(p-fluorophenyl)-8-fluoropyrazole[4,3-c]quinolin-3(5H)-one at a dose of 100 mg/Kg i.p.

Furthermore the $LD_{50}$ for 2-phenyl[4,3-c]quinolin-3(5H)-one is greater than 5000 mg/Kg p.o..

Said advantageous properties render the compounds of formula I, tautomers or pharmaceutically acceptable salts thereof especially useful for controlling food intake, suppressing appetite and treating obesity in mammals, including man.

The following examples are intended to illustrate said compositions useful in the new method according to this invention, and they are not to be construed as being limitations thereon. All parts wherever given are parts by weight, and the active ingredient is preferably 2-phenyl-pyrazolo[4,3-c]quinolin-3(5H)-one, but may also be any other compound encompassed by the above structural formula I, tautomer or salt thereof.

EXAMPLE 1

Preparation of 10,000 tablets each containing 50 mg of the active ingredient:

| Formula: | |
|---|---|
| 2-(p-fluorophenyl)-8-fluoropyrazolo[4,3-c]-quinolin-3(5H)-one | 500.00 g |
| Lactose | 707.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches, uppers bisected.

EXAMPLE 2

Preparation of 10,000 capsules each containing 20 mg of the active ingredient:

| Formula: | |
|---|---|
| 2-phenyl-pyrazolo[4,3-c]-quinolin-3(5H)-one | 200.0 g |
| Lactose | 1,700.0 g |
| Talcum powder | 100.0 g |

Procedure:

All the powders are passed through a screen with openings of 0.6 mm. Then the drug substance is placed in a suitable mixer and mixed first with the talcum, then with the lactose until homogenous. No. 3 capsules are filled with 200 mg each, using a capsule filling machine.

EXAMPLE 3

Appetite-suppressant formulations comprising e.g. about 0.1–1.0% aqueous suspensions with 3% cornstarch, as well as analogous appetite-suppressant formulations to those given in the previous examples and comprising 10 to 200 mg of certain compounds encompassed by U.S. Pat. No. 4,312,870, are similarly prepared, i.e. with the active ingredient being:
(a) 2-(p-fluorophenyl)-8-methoxypyrazolo[4,3-c]quinolin-3(5H)-one hydrochloride,
(b) 2-phenyl-8-fluoropyrazolo[4,3-c]quinolin-3(5H)-one,
(c) 2-(o-fluorophenyl)-pyrazolo[4,3-c]quinolin-3(5H)-one,
(d) 2-phenyl-7-trifluoromethylpyrazolo[4,3-c]quinolin-3(5H)-one,
(e) 2-(m-fluorophenyl)-pyrazolo[4,3-c]quinolin-3(5H)-one, (f) 2-phenyl-8-methylpyrazolo[4,3-c]quinolin-3(5H)-one, (g) 2-(2-pyridyl)-8-fluoropyrazolo[4,3-c]quinolin-3(5H)-one, (h) 2-(3-pyridyl)-pyrazolo[4,3-c]quinolin-3(5H)-one hydrochloride, m.p. 322°-325° C., or (i) 2-(3-pyridyl)-8-fluoropyrazolo[4,3-c]-3(5H)-one hydrochloride, m.p. 351°-354° C.

What is claimed is:

1. A method of suppressing appetite in mammals comprising the enteral or parenteral administration of an appetite-suppressant effective amount of a compound of the formula

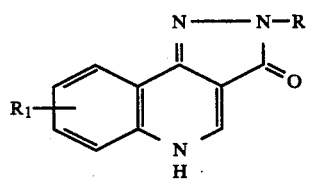

or a tautomer thereof
wherein $R_1$ is hydrogen, alkyl or alkoxy with up to 4 carbon atoms each, hydroxy, fluoro, chloro, bromo or trifluoromethyl; and R is phenyl, fluorophenyl, or pyridyl; or a pharmaceutically acceptable salt thereof; or of a pharmaceutical composition comprising a said compound in combination with a pharmaceutical carrier.

2. A method according to claim 1 comprising the enteral administration of a pharmaceutical composition as defined in claim 1.

3. A method according to claim 2 wherein $R_1$ is hydrogen; or $R_1$ is 7- or 8-(methyl, methoxy, chloro, fluoro or trifluoromethyl); and R is phenyl, fluorophenyl or 3-pyridyl.

4. A method according to claim 2 wherein $R_1$ is hydrogen or 8-fluoro; and R is phenyl or p-fluorophenyl; and the pharmaceutically acceptable salt is the sodium, hydrochloride or mesylate salt.

5. A method of suppressing appetite according to claim 2 wherein the appetite-suppressant compound is 2-phenylpyrazolo-[4,3-c]-quinolin-3(5H)-one; or the sodium, hydrochloride or mesylate salt thereof.

6. A method of suppressing appetite according to claim 2 wherein the appetite-suppressant compound is 2-(p-fluorophenyl)-8-fluoropyrazolo[4,3-c]quinolin-3-(5H)-one or the sodium, hydrochloride or mesylate salt thereof.

* * * * *